(12) United States Patent
Li et al.

(10) Patent No.: US 9,176,048 B2
(45) Date of Patent: *Nov. 3, 2015

(54) NORMAL INCIDENCE BROADBAND SPECTROSCOPIC POLARIMETER AND OPTICAL MEASUREMENT SYSTEM

(75) Inventors: Guoguang Li, Beijing (CN); Tao Liu, Beijing (CN); Edgar Genio, Beijing (CN); Tiezhong Ma, Beijing (CN); Xiaolang Yan, Beijing (CN)

(73) Assignee: BEIOPTICS TECHNOLOGY CO., LTD, Beijing (CN)

( * ) Notice: Subject to any disclaimer, the term of this patent is extended or adjusted under 35 U.S.C. 154(b) by 412 days.

This patent is subject to a terminal disclaimer.

(21) Appl. No.: 13/696,054

(22) PCT Filed: Jun. 1, 2011

(86) PCT No.: PCT/CN2011/000927
§ 371 (c)(1),
(2), (4) Date: Nov. 2, 2012

(87) PCT Pub. No.: WO2011/150680
PCT Pub. Date: Dec. 8, 2011

(65) Prior Publication Data
US 2013/0050702 A1    Feb. 28, 2013

(30) Foreign Application Priority Data
Jun. 2, 2010    (CN) .......................... 2010 1 0199230

(51) Int. Cl.
*G01J 4/00*    (2006.01)
*G01N 21/21*    (2006.01)
*G01J 3/02*    (2006.01)

(52) U.S. Cl.
CPC ................. *G01N 21/211* (2013.01); *G01J 3/02* (2013.01); *G01J 3/021* (2013.01); *G01J 3/0208* (2013.01); *G01J 3/0224* (2013.01); *G01N 21/21* (2013.01)

(58) Field of Classification Search
CPC ................. G01N 2021/213; G01N 2021/214; G01N 21/211; G01N 21/21; G01J 3/447; G01J 4/04; G01J 3/0224; G01J 4/00; G01J 3/021; G01J 3/0208; G01B 2210/56; G01B 11/0641

See application file for complete search history.

(56) References Cited

U.S. PATENT DOCUMENTS

| 4,285,596 | A |   | 8/1981 | Landa |
| RE32,660 | E | * | 5/1988 | Lindow et al. ................. 250/225 |
| 4,878,756 | A | * | 11/1989 | Stauffer ........................ 356/406 |
| 5,608,526 | A |   | 3/1997 | Piwonka-Corle et al. |
| 2003/0006385 | A1 | * | 1/2003 | Banks ......................... 250/559.4 |

FOREIGN PATENT DOCUMENTS

CN    101427911 A    5/2009
JP    4138339 A    5/1992

OTHER PUBLICATIONS

P.R. China, State Intellectual Property Office, International Search Report for International Application No. PCT/CN2011/000927, mailed Sep. 8, 2011.

* cited by examiner

*Primary Examiner* — Kara E Geisel
*Assistant Examiner* — Rufus Phillips
(74) *Attorney, Agent, or Firm* — Bright IP Law Offices (57) ABSTRACT

A kind of normal incidence broadband spectroscopic polarimeter which is easy to adjust the focus, has no chromatic aberration, maintains the polarization and has simple structure. The normal incidence broadband spectroscopic polarimeter can make the probe beam normal incidence and focus on the sample surface by using at least one flat reflector element to change propagation direction of the focused beam. Moreover, the normal incidence broadband spectroscopic polarimeter contains at least one polarizer as to measure the anisotropy or non-uniform samples, such as three-dimensional profile and material optical constants of thin films consisting of the periodic structure. An optical measurement system including the normal incidence broadband spectroscopic polarimeter is also provided.

26 Claims, 7 Drawing Sheets

NORMAL INCIDENCE BROADBAND SPECTROSCOPIC POLARIMETER AND OPTICAL MEASUREMENT SYSTEM

CROSS REFERENCE TO RELATED APPLICATIONS

This application is the U.S. National Stage of International Patent Application No. PCT/CN2011/000927 filed on Jun. 1, 2011, which claims priority to Chinese Patent Application No. 201010199230.7 filed on Jun. 2, 2010. Both the PCT Application and Chinese Application are hereby incorporated by reference in their entirety.

FIELD OF THE INVENTION

The invention relates to a normal incidence broadband spectroscopic polarimeter containing at least one polarizer. More specifically, by using at least one flat reflector element to change the propagation direction of the focused beam, the probing beam can focus on the surface of the sample at normal incidence, in addition, the invention relates to the optical measurement system including such normal incidence broadband spectroscopic polarimeter.

BACKGROUND OF THE INVENTION

Figure 1:
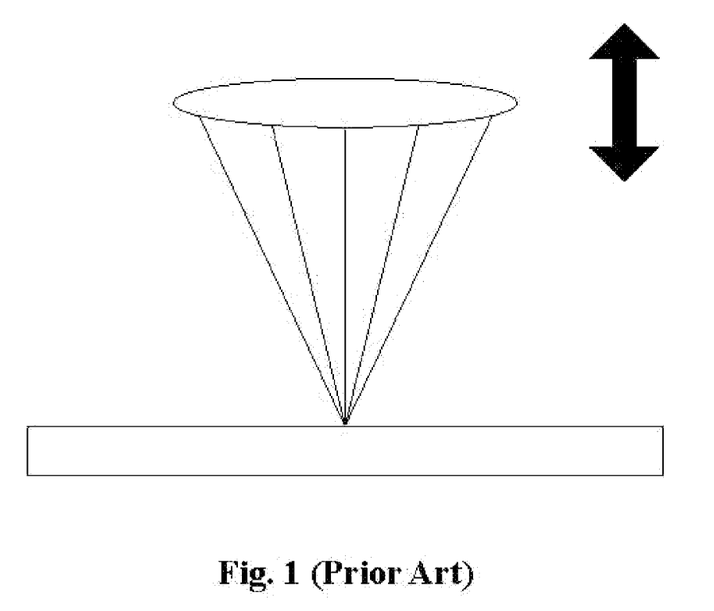
FIG. 1 is a schematic drawing to illustrate the realization of the focus by moving up and down the last focusing lens.
Figure 2:
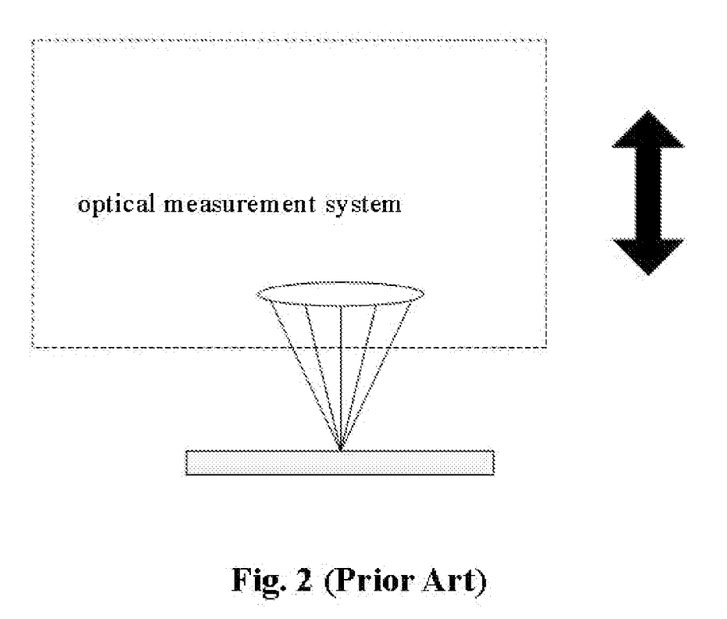
FIG. 2 is a schematic drawing to illustrate of the realization of the focus by moving the entire optical system.

Generally, a key step in optical measurement technique is to make the probing beam focused onto the sample. Two methods are currently widely used. One method is to separate the last focusing lens from other components and only to adjust the focusing lens to focus the probing beam onto the sample. An example was illustrated in FIG. 1, the focusing is achieved by moving the last focusing lens up and down. The other method is to adjust the whole optical measurement system to focus the probing beam on the sample. For example, as shown in FIG. 2, the focusing is achieved by moving the whole optical system up and down (refer to the U.S. Pat. No. 5,747,813 and U.S. Pat. No. 5,486,701).

With the rapid development of semiconductor industry, it becomes very critical to apply optical technology to accurately measure the critical dimension (CD), spatial profile and material properties of three-dimensional structures formed by the single or multiple layer on wafers. While detecting 150 mm, 200 mm and 300 mm wafers, its surface may not be flat due to various reasons such as film stress. Therefore, autofocusing for each measurement point is a key technique to achieve high accuracy and rapid measurement and ensure production of semiconductor production line across the whole wafer. And it is widely known that focusing the broadband probing beam into a small spot size on the sample surface is highly desired. The small spot size allows to measure the micro patterned structures and broadband spectrum is helpful for better measurement accuracy. There were some issues for the first approach in this case: lens usually has chromatic aberration which results in different wavelengths of light focusing on different locations and thus worsen the accuracy. It is also hard to find the lens materials with good transmission in the whole broadband wavelength range. The second approach inherits the same problem of lens aberration and has additional technical challenges. It is not a trivial job to adjust the entire optical system to focus and precise measurement is therefore difficult to be achieved.

A new approach was proposed as the above reasons, that is, focusing the broadband probe beam on the sample surface by using the curved mirrors (for example, refer to U.S. Pat. No. 5,608,526 and U.S. Pat. No. 7,505,133B1, U.S. Patent Application Publication No. 2007/0247624A1 and Chinese patent application Publication No. 101467306A). This method has advantages as below: the reflector mirror does not produce chromatic aberration in whole wavelength range, and has high reflectivity in wide wavelength range.

However, although the application of curved mirrors does not produce chromatic aberration and thus improve the focus and the accuracy, compared with lens, it is more difficult to align the optical path with curved mirrors. The adjustment of focal point and spatial orientation of curved mirrors was constrained by the incident light, often requiring the simultaneous adjustment of the entire optical system for better control of the output optical path and focusing point. For example, (1) elliptical mirror: While the spatial location of two focusing point is relatively fixed, the adjustable range of optical path and focusing position is very limited by adjusting the individual elliptical mirror after the incident light path was corrected. (2) Toroidal mirror: Although the two corresponding focusing points can be achieved in a certain range of incident angles, the spatial relationship of the two focusing points changes with the relationship between toroidal mirror and incident light. The correlations between two focusing points are complex and it is very difficult to achieve focusing. Another drawback is that its adjustable range is small and is easy to create image aberrations. (3) Off-axis parabolic mirrors: The adjustable range was very limited because the aberrations were resulted as the angle of off-axis parabolic mirrors changes relative to the direction of incident light. While a wide range of the focusing position can be achieved by moving the off-axis parabolic mirror along with the direction of the collimated light beam, the relative position of focusing point to the off-axis parabolic mirror center cannot be changed. This also limits the adjustable range of the focusing points. In summary, the use of a single curved mirror itself does not produce chromatic aberration, but it is difficult to control the direction of the optical path and focusing positions. Furthermore, the polarization of beam will be changed after reflected by a single mirror. Take an aluminum reflector mirror as an example, the reflection coefficient $r_s$ and $r_p$ of S and P polarized light were changed with the incident angle, the amplitude and phase difference between the S and P polarized light vary with the angle and the wavelength of incident beam. In short, because the polarization states S and P with the polarization direction orthogonal to each other have different reflectivity and phase change, after being reflected by a mirror, the polarization states of broadband beam varies, resulting the control of the change of beam polarization difficult (for example, refer to U.S. Pat. No. 6,829,049B1 and No. 6,667,805).

In addition, the beam polarization control capability of the spectrometer determines the scope of its applications. Take Optical Critical Dimension (OCD) equipment as an example. Such equipment is widely used in integrated circuit manufacturing lines for process controls. The OCD tools can measure the critical dimension (CD), three-dimensional profile of periodic pattern on sample surface, thickness and optical constants of multilayer film materials by collecting reflectance spectra and phase characteristics of the polarized beam from the sample surface and fitting numerical simulation results. For this kind of applications, the focusing system of spectrometer must be able to control the beam polarization in the process of focusing and optical signal collection.

Furthermore, when the spectrometer without polarizer was used to measure the sample with periodic structures, as mentioned in China patent application No. 201010270454.2, the incident beam must be natural light because the rotation angle of incident beam cannot be adjusted relative to the anisotropic angle of samples. In theory, the natural light emitted from light source is required to arrive on the sample surface either maintaining absolutely polarization or passing through none of polarization components. The anisotropic samples cannot be measured if polarization states were not maintained; under this circumstance, the measured values change as the anisotropic samples rotate. Therefore, the spectrometer capable of measuring the anisotropic samples while without polarization control components included demands the high quality of optical elements and the sophisticated adjustment of the optical path. The light reflected by the sample is partially polarized; starting from the light source to the detector, in theory, the polarization of the incident beam either was maintained completely or no polarization-sensitive component was present in the path. For example, if a polarization sensitive component was encountered in the path, a depolarizer is required, thus it will reduce the signal to noise ratio. Moreover, the above problem cannot be corrected by numerical methods.

SUMMARY OF THE INVENTION

In view of the above issues, a normal incidence broadband spectroscopic polarimeter has been brought forward by the inventor of the invention. The normal incidence broadband spectroscopic polarimeter has the following key features: 1). the focus is easily adjusted, 2). no chromatic aberration is introduced, 3). the polarization properties are maintained, and 4). structure is simple. The ellipsometer contains at least one polarizer to perform high-accuracy measurement of the anisotropic and/Of inhomogeneous samples, such as three-dimensional profile and material optical constants of thin films within periodic structures.

The present invention provides a normal incident broadband spectroscopic polarimeter including a light source, a beam splitting element, a focusing unit, a polarizer, a first curved reflector element, a first flat reflector element and a detection unit, wherein: the beam splitting element set in an optical path between the light source and the focusing unit, and the beam splitting element is used to pass through a part of the beam from the light source before incident on the focusing unit, and receive the beam reflected from a sample, and in turn passing through the flat reflector element, the first curved reflector element, the polarizer and the focusing unit and then reflect the beam to the detection unit; the focusing unit is used to receive a beam passing through the beam splitting element and converge the beam into a collimated beam; the polarizer set between the focusing unit and the first curved reflector element, and the polarizer is used to pass through the collimated beam and incident on the first curved reflector element; the first curved reflector element is used to receive the collimated beam of the polarizer and to converge the beam into a focused beam; the first flat reflector element is used to receive the focused beam and reflect the focused beam and make it normal incidence on the sample, as well as focus on the sample; and the detection unit is used to detect a beam reflected from the sample, and in turn passing through the first flat reflector element, the first curved reflector element, the polarizer and the focusing unit and reflected by the beam splitting element.

The first flat reflector element and the first curved reflector element may have the same reflective material and coating structure and meet the conditions that the incident angles of beam are the same and the incident planes are perpendicular to each other.

The beam splitting element can be Beam-splitting prism, Beam-splitting plate, Polka-dot Beamsplitter or Pellicle Beamsplitter. For example, the beam splitting element can be Daheng optics GCC-401, Daheng optics GCC-411, Edmund Polka-dot Beamsplitter, Newport Polka-dot Beainsplitter, or Edmund Pellicle Beamsplitter.

In present invention, the polarizer can be thin-film polarizer, Glan-Thompson prism polarizer, Rochon prism polarizer, Glan-Taylor prism polarizer, Glan laser polarizer. In particular, the preferred polarizer is a Rochon prism polarizer and its material is preferred to be $MgF_2$.

The present invention also provides an optical measurement system which includes the normal incidence broadband spectroscopic polarimeter.

A further understanding of the nature and advantages of the inventions herein may be realized by reference to the preferred embodiment of remaining sections of the specifications and the attached drawings.

BRIEF DESCRIPTION OF THE DRAWINGS

In the attached drawings, all of them are not on scale and the same reference signs in different drawings always represent basically the same elements. The same reference sign with different letter suffix represents the instances of basically the same components.

DETAILED DESCRIPTION OF THE EMBODIMENTS

The terminologies in the article are used only for the purposes of described, not for restrictive purposes. Unless otherwise stated, the terminologies used in this invention are consistent with their generic meanings.

(Focus Principle)

As stated above, although the use of curved mirror itself does not produce chromatic aberration, it is difficult to adjust and to control the direction of the light path and the focusing position by simple adjustment of optical components. In view of these problems, a new method of using flat mirrors is proposed by the inventor of this invention to adjust focusing points.

Figure 3:
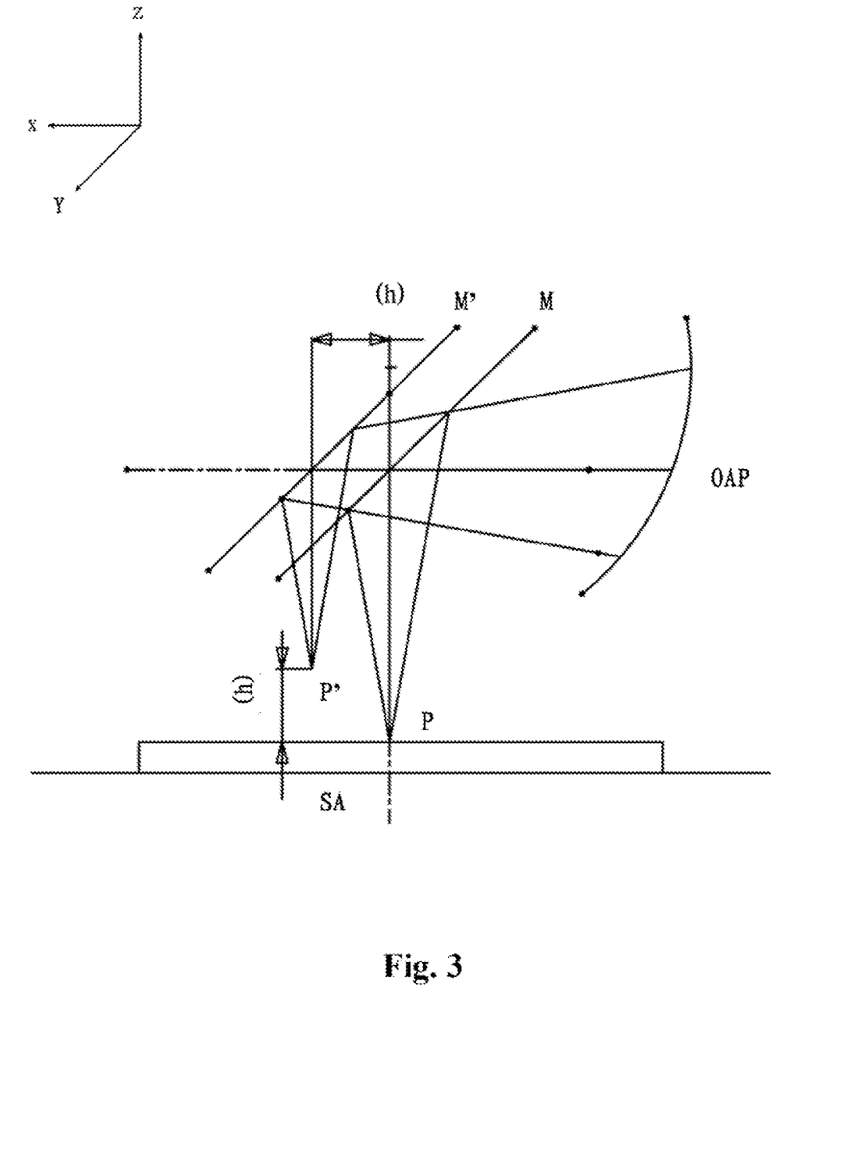
FIG. 3 is a schematic drawing to illustrate the realization of the focus by moving the flat mirror.

As shown in FIG. 3, assuming that: the focused beam from off-axis parabolic mirror OAP focus on the position P of sample SA after reflected by flat mirror M, the chief ray propagates along the horizontal and the incident angle of the chief ray on the flat mirrors is 45 degrees. When the flat mirror M moves distance h along optical transmission direction of the chief ray of the focused beam (i.e., flat mirror is moved to the position M'), the focusing point P' of the focused beam from off-axis parabolic mirror OAP after reflected h flat mirror M relative to the original focus position P moves distance h in vertical direction, as well as in the propagation direction of the chief ray. If the focusing point on the samples needs to move upward by distance h, one only needs to move the flat mirror M further also by the distance h relative to the off-axis parabolic mirror OAP, while moving the sample platform by the same distance h along the moving direction of the flat mirror M. Therefore, the focus position of the light beam can be easily adjusted to adapt to the change of the sample height.

Since the flat mirror does not affect the focus condition of incident light and produce chromatic aberration, the use of reflecting mirror can maintain the beam quality while changing the beam propagation direction. In addition, on one hand, flat mirrors are often used in folding optical path to make the whole optical system more compact. On the other hand, flat mirrors can realize high reflectivity in broadband spectral range and have little influence on the light intensity; and with the aid of the focus judgment method, flat mirrors can realize the accurate manual or automatic focusing. Therefore, in present invention, the focus was realized by adjusting the flat mirror.

(The Principle of Maintaining the Polarization Properties of Arbitrarily Polarized Light)

Figure 8:
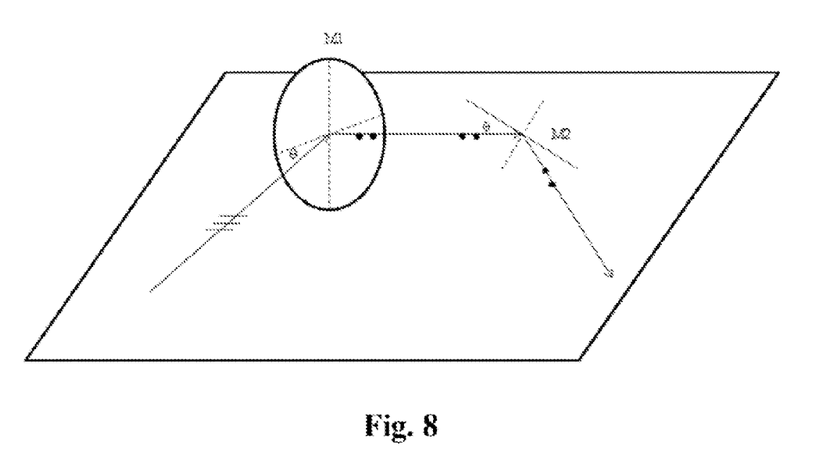
FIG. 8 to FIG. 10 are the schematic drawings for maintaining polarization state of an optical beam.
Figure 9:
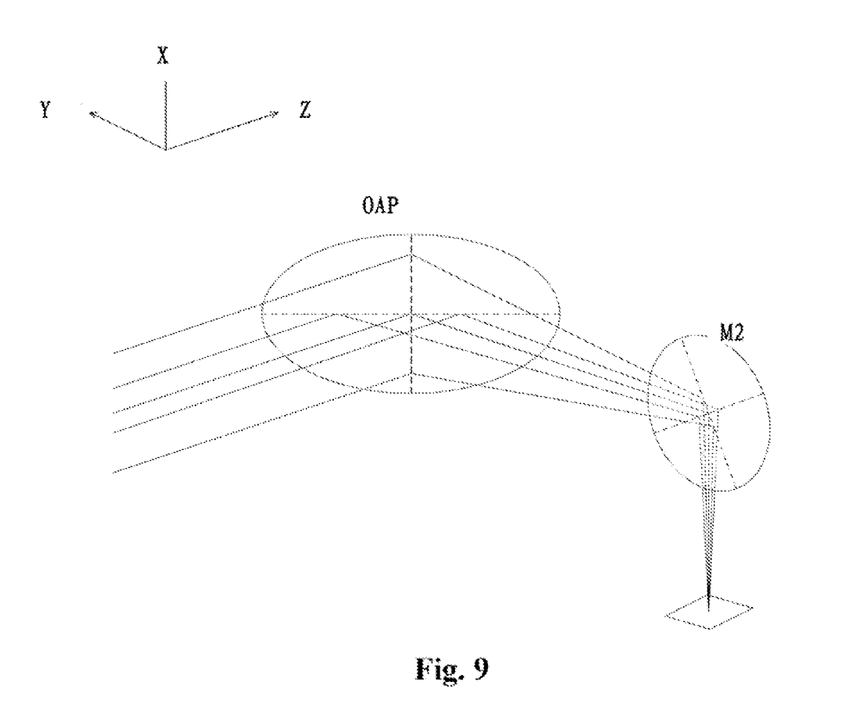

With reference to FIGS. 8 and 9, the basic principles of maintaining polarization properties of polarized light through two flat mirrors or a flat mirror and an off-axis parabolic mirror can be explained as below.

As shown in FIG. 8, assume that the S (or P) polarized beam with the incident plane of the first flat mirror M1 as reference enters M1 with the incident angle of (90−θ) and is reflected by the second flat mirror M2 by the first flat mirror M1. If the incident plane on the first flat mirror M1 is perpendicular to the incident plane on the second flat mirror M2, and M2 is tilted to meet the beam reflected by M1 incident on M2 with the incident angle of (90−θ), the S (or P) polarized light with the incident plane of M1 as reference will change into P (or S) polarized light with the incident plane on M2 as reference after being reflected by M1.

Now analyze the changes of the propagation direction and the polarization state of the beam with the right-hand reference system established by taking the beam propagation direction as +Z direction. The above process can be expressed into a mathematical formula below:

$$\begin{cases} Ex = E_{1s} \\ Ey = E_{1p} \end{cases} \quad (a)$$

The polarization components $E_{1s}$, $E_{1p}$ with the incident plane on M1 as the reference are defined as +X and +Y direction component in the right-handed reference system, respectively. After being reflected by M1, $$\begin{cases} E'_{1s} = r_{1s} E_{1s} \\ E'_{1p} = r_{1p} E_{1p} \end{cases} \quad (b)$$

$E_{1s}'$, $E_{1p}'$ represent the polarized components of reflected light with the incident plane on M1 as reference; $r_{1s}$ and $r_{1p}$ represent the reflectance of S- and P-polarized lights on the first flat mirror respectively, with incident plane on M1 as reference and incident angle of (90-θ). And, $$\begin{cases} E_{2s} = E'_{1p} \\ E_{2p} = E'_{2s} \end{cases} \quad (c)$$

After reflected by M1, the $E_{1s}'$ and $E_{1p}'$ become the incident lights of M2 with the polarization components $-E_{2p}$ and $E_{2s}$, respectively, with the incident plane of M2 as reference. After reflected by M2, $$\begin{cases} E'_{2s} = r_{2s} E_{2s} \\ E'_{2p} = r_{2p} E_{2p} \end{cases} \quad (d)$$

$E_{2s}'$, $E_{2p}'$ represent the polarization components of reflected light with the incident plane of M as reference, $r_{2s}$ and $r_{2p}$ represent the reflectivity on the second mirror M2 of the S-polarization and P-polarization respectively, which enter M2 with angle of (90-θ) and take incident plane of M2 as reference.

Due to the right-hand rule, the polarization direction of S-polarized light which takes incident plane of M1 as reference is the negative direction of the P-polarized light which takes incident plane of M2 as reference. Set the polarization direction of S-polarized beam which takes incident plane of M1 as reference is always along the positive direction of X-axis in the right-hand reference system which is established by taking the beam propagation direction as +Z direction. After the beam is reflected by M2, the polarization direction of P-polarized beam, with incident plane of M2 as reference, is in the positive direction of X-axis; so, the polarization direction of S-polarized beam, with incident plane of M2 as reference, is in the negative direction of Y-axis. Thus:

$$\begin{cases} E'_{2p} = E'_{s} \\ E'_{2s} = E'_{y} \end{cases} \quad (e)$$

$E_{1s}'$ and $E_{y}'$ represent the polarization components of reflected beam. When M1 and M2 have the same reflective materials and coating structure:

$$\begin{cases} r_{1s} = r_{2s} \\ r_{1p} = r_{2p} \end{cases} \quad (f)$$

Based on the above formulae, there is:

$$\begin{cases} \dfrac{E_s}{E_y} = \dfrac{E'_s}{E'_y} \end{cases} \quad (g)$$

In the above formulae (a)-(g), all the variables are complex. The formula (g) shows that the polarization component ratio of reflected light equals to that of the incident light. Therefore, with the above two flat mirrors, the polarization properties of polarized light can be maintained.

According to the above formulae (a)-(e), it is known as long as the first flat mirror M1 and the second flat mirror M2 satisfy the relation of $r_{2s}r_{1p}=r_{2p}r_{1s}$, the relationship in formula (g) can be maintained. That is, if two mirrors satisfy the relation $r_{2s}r_{1p}=r_{2p}r_{1s}$, then through the two mirrors, polarization properties of polarized light can be maintained.

Therefore, in the system consisting of two flat mirrors with the incident plane perpendicular to each other and with the same incident angle, the polarization characteristics of the incident light can be perfectly maintained. With an assumption that one of the above two flat mirrors was replaced with an off-axis parabolic mirror which has the same reflective material and coating structure as the other flat mirror, the two mirror system was simulated for the case of small numerical aperture (NA). Although the polarization properties of the beam will have deviations after passing the system constituted. by the off-axis parabolic mirror and flat mirror, when the collimated beam is focused. with a small NA, the deviations of the polarization are not sufficient to affect the accuracy of measurement. For the strict polarization requirement, the measurement results can be further calibrated using numerical calculations.

Figure 10:
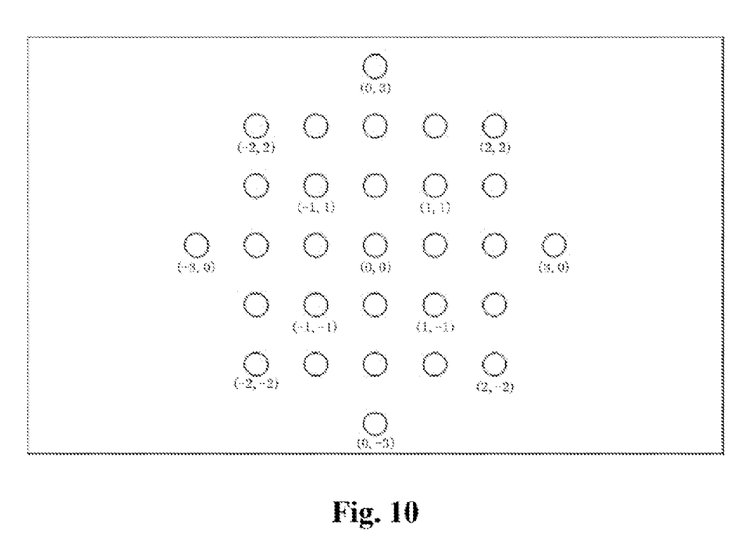

For example, as shown in FIG. 9, a collimated beam is a circularly polarized light before being incident onto the off-axis parabolic mirror GAP, i.e., Ex=Ey, and Phase (Ex)– Phase (Ey)=90 degrees, wherein, Ex and Ey are the amplitude of the electric vector of the beam in the x and y directions respectively, and Phase (Ex) and Phase (Ey) are the phase of the electric vector of the beam in the x and y directions respectively. After reflected by off-axis parabolic mirrors, the half-cone angle of focused beam is 4.2 degrees (NA=0.073). When the wavelength of incident light is 210 nm, the calculated point distribution within the cross-sectional of incident beam is shown in FIG. 10 (29 points in total and already partially marked, for example, (0, 3) to (0, 0)). After numerical calculation, the intensities and phase changes of polarization in the focus point are listed in Table 1. Polarization intensity variation is defined as |Ex/Ey|~1, and the polarization phase variation is defined as Phase (Ex)–Phase (Ey)–90. Because the intensity and phase variations of the polarized beam with a central symmetry of (0, 0) are quite closely complementary, the above variations as a whole can be further alleviated.

TABLE 1

| Calculated points | Polarization intensity variation | Polarization phase variation (degree) | Calculated points | Polarization intensity variation | Polarization phase variation (degree) |
|---|---|---|---|---|---|
| (−3, 0) | 0.0011 | 2.1107 | (3, 0) | −0.0069 | −2.6477 |
| (−2, −2) | 0.0205 | 2.3577 | (2, 2) | −0.0244 | −2.1827 |
| (−2, −1) | 0.0106 | 1.8931 | (2, 1) | −0.0145 | −1.9597 |
| (−2, 0) | 0.0014 | 1.4637 | (2, 0) | −0.0039 | −1.7022 |
| (−2, 1) | −0.0071 | 1.0695 | (2, −1) | 0.0073 | −1.4099 |
| (−2, 2) | −0.0150 | 0.7107 | (2, −2) | 0.0193 | −1.0827 |
| (−1, −2) | 0.0212 | 1.5870 | (1, 2) | −0.0211 | −1.3694 |
| (−1, −1) | 0.0107 | 1.1563 | (1, 1) | −0.0117 | −1.1123 |
| (−1, 0) | 0.0010 | 0.7607 | (1, 0) | −0.0017 | −0.8203 |
| (−1, 1) | −0.0080 | 0.4004 | (1, −1) | 0.0091 | −0.4934 |
| (−1, 2) | −0.0164 | 0.0752 | (1, −2) | 0.0206 | −0.1315 |
| (0, −3) | 0.0329 | 1.1893 | (0, 3) | −0.0266 | −0.8739 |
| (0, −2) | 0.0212 | 0.7579 | (0, 2) | −0.0184 | −0.6175 |
| (0, −1) | 0.0102 | 0.3614 | (0, 1) | −0.0095 | −0.3263 |
| (0, 0) | 0.0000 | 0.0000 | | | |

Therefore, the system with the off-axis parabolic mirror and flat mirror can also maintain the polarization properties of polarized light.

The above example only simulated the condition of replacing one of the two flat mirrors with an off-axis parabolic mirror with the same reflective material and coating structure. Not only flat mirror with off-axis parabolic mirror, but also other curve mirror, such as toroidal mirror, ellipsoidal mirror or non-quadric surface mirror, can the polarization properties of polarized light be essentially maintained as long as any two kinds of mirrors meet the above relations.

In summary, if the two mirrors have approximately same reflective material and coating structure and meet the conditions that incident angles of the chief ray are the same and the incident planes of the chief ray are perpendicular to each other (with in the allowed error range, that is, including the situation that incident angles are approximately the same and incident planes are nearly perpendicular to each other), the polarization characteristics of arbitrary polarized light will remain unchanged after reflected by the two mirrors. The example of mirrors with the same reflective material and coating structure are the mirrors simultaneously coated in the same vacuum chamber.

In addition, in the case that the two mirrors do not have the same reflective material and coating structure and only meet the conditions of the beam incident planes perpendicular or parallel to each other, only when the probe beam is linearly polarized and the polarization direction is perpendicular or parallel to the incident plane, the polarization state can be remained unchanged.

(The Methods for Focusing Control and Judgment)

As described below, in the broadband spectroscopic polarimeter of the present invention, there are two was to achieve focus.

The first method is to observe the changes of signal intensity of collected reflected light. Compared to the focused state, defocus state will result in the loss of peripheral part of the light spot in the optical collection system after the location of spectrograph slit is calibrated. After rough focusing process, the most accurate focus can be obtained by finding the maximum intensity of optical signal. The mathematical methods and basic steps of quickly finding the focus are as follows: in the vicinity of focus, the relationship between the optical signal intensity with defocus distance is approximated by a quadratic. curve type, i.e., the parabola: $I=-A(x-x_0)^2+B$, wherein, I is optical signal intensity, $x_0$ is focus position. A and B are the coefficients. In the process of auto-focus, according to measurement value of the first three different locations (i.e., A, B and C position), the maximum location of the quadratic curve can be obtained by curve fitting; take the measured value from this position as the newly added data point, and fit curve again; iterate this procedure until the fitting meets the formula $|x_{n+1}-x_n|<\sigma$ theoretically, therein $x_0$ is the focusing position of the nth trine, $x_{n+1}$ is the focus position of curve fitting of (n+1)th time obtained when the measured value at the focus position of nth times is added, and σ is the adjustable parameter for the accuracy of the system.

The second method is to observe the clarity of imaging of the sample surface in the pattern recognition system. In an ideal focus state, after the location of pattern recognition system is calibrated, the image shall be the clearest if the sample surface is in focus. For a given image resolution, image clarity is determined by the sharpness of image. The sharpness was the contrast of the image edge. More precisely, the sharpness is the amplitude of the brightness derivative in space. After the coarse focus was achieved, (i.e., the sample surface can be identified in pattern recognition system), the image clarity can be simultaneously calculated through the focus adjustment. So, with the assistance of above mathematical methods and the basic steps of finding the coarse focus, the most accurate focus can be obtained.

(Polarizer)

Polarizer used in the present invention can be Rochon prism polarizer RP, for example, PUM and PUM2 Rochon prism of the B. Halle Nachfl GmbH. The material of Rochon prism polarizer can be MgF2, a-BBO, Calcite, YVO4 or quartz. By using birefringent crystal (the refractive indices of ordinary light and extraordinary light are different). Rochon prism polarizer make the two orthogonal polarized beams of incident beam exit from Rochon prism interface with a certain angle, wherein the direction of ordinary light remains the same as the incident direction, and exits with the state of linearly polarized light Different materials have different transmission spectral range; for MgF2 the spectral range can be achieved in 130-7000 nm. Since the refractive indices of ordinary light and extraordinary light are different for different materials, the angle between the o light and $e_{1s}$ light of transmitted light is different as well. For example, for $MgF_2$ or quartz, the angle difference between o light and e light is 1~2 degrees, however, for the a-BBO or YVO4, the difference is up to 8~14 degrees. This angle also partly depends on the cutting angle of the Rochon prism. After the probe beam transmitted through the polarizer, the o light has the angle of incident normal to the sample, whereas the e light is at an oblique incident angle on the sample; when the reflected e light from the sample surface enters into the area of the optical aperture of the polarizer, the reflected e light may enter into the same polarizer at the same time, and then reaches the detector, thus affects the measurement. For a polarizer with large e light deviation angle, the reflected e beam from the sample surface is hard to re-enter the polarizer, in order to improve the measurement accuracy, an aperture can be set at a position above the sample surface where the o light and e light are separated to avoid the e light entering on the sample surface or being reflected back to the polarizer from the sample surface.

(Measuring Principle)

(1) Absolute reflectivity measurement method: measure the absolute reflectance of sample in two orthogonal directions of polarization state. The absolute reflectance of a sample can be measured as follows:

a, Measure the dark values $I_d$ of a spectrometer;

b, Measure the reflectance of a reference sample, for example, the bare silicon wafer, and obtain the spectrum $I_r$;

c, Measure the sample and obtain the spectrum I;

Thus, the reflectance of the sample is:

$$R(I-I_d)/(I_r-I_d) \times R(\text{ref})$$

Wherein, R(ref) is the absolute reflectance of the reference sample. R(ref) can be obtained from other measurements, or through calculating the characteristics of the reference sample; R(ref) is usually from the reflectivity of bare silicon.

Figure 11:
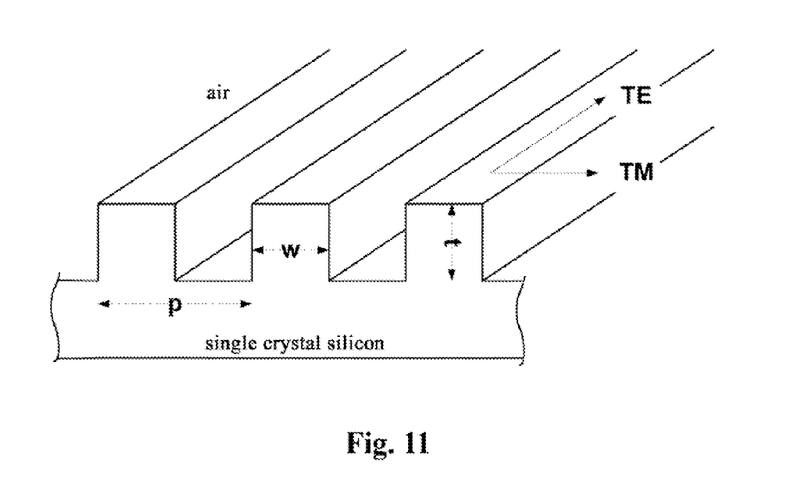
FIG. 11 is a block diagram of periodic shallow trench structure on single crystal silicon.
Figure 12:
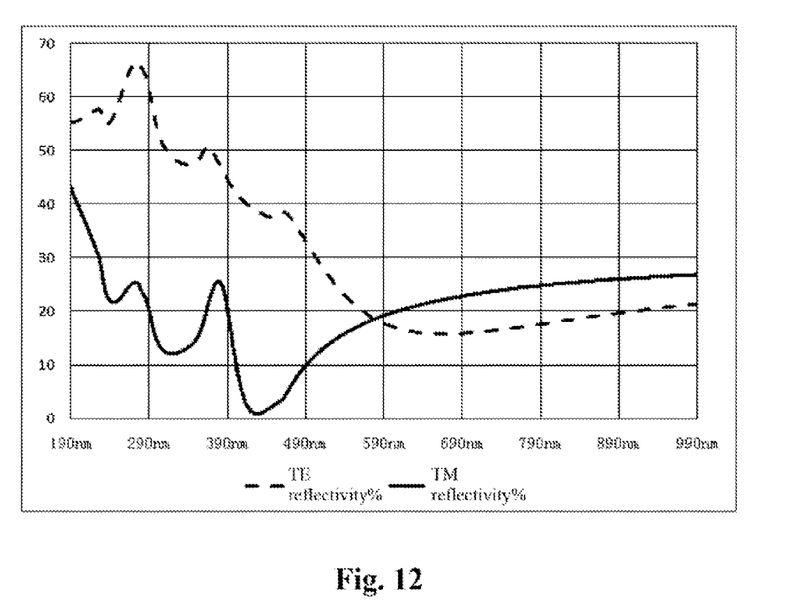
FIG. 12 is a schematic drawing to show the absolute reflectance spectra of TE and TM mode from single crystal silicon periodic shallow trench.

In periodic shallow trench structure, as shown in FIG. 11, the two orthogonal polarization directions are defined respectively as the direction perpendicular to the linear structure of TM and parallel to the linear structure of the direction of TE. FIG. 12 shows the reflectivity of the structure with the pitch of the 100 nm, line width w of 50 nm, groove depth t of 50 nm, wherein the dotted line for the reflectivity of TE polarization, the solid line for the reflectivity of TM polarization.

(2) Ellipsometry measurement method: the normal incidence broadband. spectroscopic polarimeter in present invention is equivalent to an ellipsometer with a structure of polarizer—sample—analyzer (PSA), in which the analyzer and the polarizer device are the same polarizer. Anisotropic medium, such as the periodical shallow trench structure shown in FIG. 11, can be calculated by ellipsometry method. In the TE and TM polarization state, the ratio of TM and TE reflectivity amplitude and phase difference caused by sample can be calculated by ellipsometry. The detailed measurement principles can be referred to HANDBOOK OF ELLIPSOMETRY, Harland G. Tompkins, 2005 and Spectroscopic Ellipsometry Principles and Applications, Hiroyuki and Fujiwara, 2007 and U.S. Pat. No. 7,115,858B1 and U.S. Pat. No. 7,330,259B2. The following are brief descriptions of the principles. The whole optical process is given by the Jones matrix, $$i(\text{out})=J_A R(A) J_S R(-P) i(\text{in}),$$

wherein, $$J_s = \begin{pmatrix} r_{xx} & r_{xy} \\ r_{yx} & r_{yy} \end{pmatrix}$$

is Jones matrix of sample reflection, x and y are two orthogonal polarization directions.

For the condition that A=P, $r_{xy}+r_{yx}=0$ (for example, refer to Li Lifeng, J. Opt, Soc Am A17, 881 (2000)), the above equation can be simplified as follows:

$$I = I_0[r_{xx}^2 \cos^4 p + r_{yy}^2 \sin^4 p + 2(r_{xx}r_{yy})^{1/2}\cos\Delta \sin^2 p \cos^2 p] =$$

$$I_0 r_{xx}^2 \begin{bmatrix} \dfrac{3\tan^2\phi + 3 + 2\tan\phi\cos\Delta}{8} + \cos(2p)\dfrac{\tan^2\phi - 1}{2} + \\ \cos(4p)\dfrac{\tan^2\phi + 1 - 2\tan\phi\cos\Delta}{8} \end{bmatrix} =$$

$$a_0 + a_2\cos(2p) + a_4\cos(4p)$$

wherein, $$a_0 = I_0 r_{xx}^2 \dfrac{3\tan^2\phi + 3 + 2\tan\phi\cos\Delta}{8}$$

$$a_2 = I_0 r_{xx}^2 \dfrac{\tan^2\phi - 1}{2}$$

$$a_4 = I_0 r_{xx}^2 \dfrac{\tan^2\phi + 1 - 2\tan\phi\cos\Delta}{8}$$

$a_0$, $a_2$, and $a_4$ are the Fourier coefficients and can be calculated from the Fourier expansion or the linear fit. $\Delta$ is the phase difference between x and y polarized fight caused by the sample reflection, $R_{xx}$ is reflectivity, $r_{xx}$ is reflection constant, $\tan \phi = |r_{xx}/r_{yy}|$. The above process leads to:

$$\tan\phi = \sqrt{\dfrac{a_0 + a_2 + a_4}{a_0 - a_2 + a_4}}$$

$$\cos\Delta = \dfrac{-a_0 + 3a_4}{\sqrt{(a_0 + a_4)^2 - a_2^2}}$$

Figure 13:
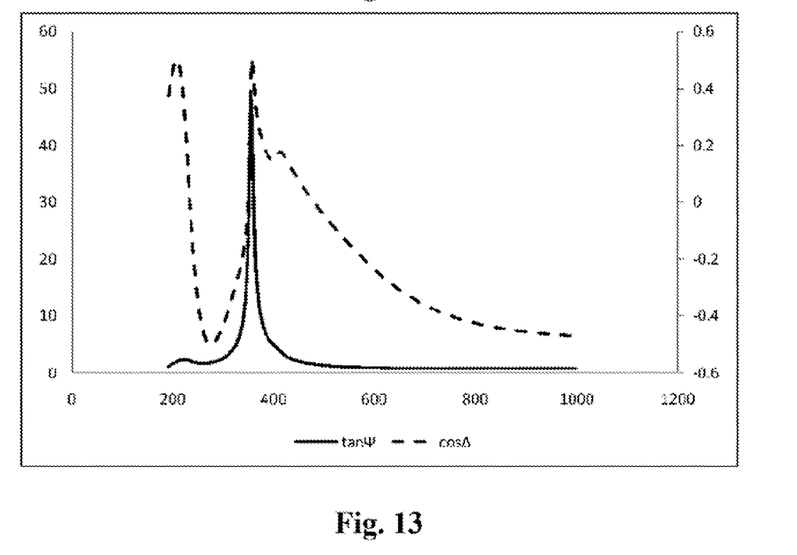
FIG. 13 is a schematic drawing to show the spectra of the reflectivity amplitude ratio of the TE and TM modes and the phase difference between the TE and TM modes in ellipsometry measurements.

The detailed process of ellipsometry method includes the following three main steps: 1) since there are rotating parts and polarization sensitive components in the system such as polarizer and detector, the system needs to be calibrated to exclude measurement deviation of light intensity caused. by the rotating parts and polarization sensitive components. Correction can be conducted by measuring the light intensity of a homogeneous sample in different polarizer angles from a standard homogeneous sample such as silicon wafer. In theory, the intensity should be identical; the change of light intensity with different angle can be used as the reference value. The ratio at different angles can be used to exclude the effect of light intensity variation in different polarizer angle of system. Specifically, rotate polarizer by 1 degree and record the intensity spectra of light reflected by silicon wafer; then complete 360-degree scan and store these data as reference value. 2) In the process of measurement, compare the intensity of reflected light at all angles with the reference value, then. obtain the relative real value of light intensity at various angles. 3) Based on the above formula to calculate the Fourier coefficients, and then the spectra of the TM/TE amplitude ratio and the phase difference between the TM and TE can be obtained. Take the structure shown in FIG. 11 as an example, the spectra are shown in FIG. 13.

After the TE and TM absolute reflectivity or the amplitude ratio and phase difference of the TM/TE are obtained by measurement, the critical dimension and three-dimensional profile of the periodically patterned sample surface, and film thickness and optical constants of multilayer materials can be derived, by comparing the measurements with the numerical simulation results. through numerical regression. In this case, the normal incidence broadband spectroscopic polarimeter can also include a computing unit; the computing unit is to do curve regression fit of the mathematical model of reflectivity and calculate the optical constants and film thickness and/or the critical dimension properties or three-dimensional profiles of the periodic structure of the sample. At present, the common method for electromagnetic wave simulation and calculation of a periodic structure is RCWA (Rigorous Coupled-Wave Analysis), and the common regression algorithm is Levenberg-Marquardt algorithm.

Besides the theoretical methods for measurement proposed in this invention, the measurement process also involves processing the variations caused by polarization sensitivity such as polarizer rotation. Such problems can be resolved by numerical method, more detailed description can be referred, to U.S. Pat. No. 6,522,406B1 and U.S. Pat. No. 6,665,070B1. With this embodiment, the linear polarization direction of the beam passing through polarizer is determined by the polarizer rotation angle; the beam entering the polarizer can be in arbitrary polarization state. When the absolute reflectance measurement method is used, the beam reflected by sample is polarized light after passing through the polarizer; in the process of being incident onto the detector, the light reflected by the reference samples and measuring samples are experiencing the same change of polarization, so it is not required to keep polarization state and thus the polarization sensitive components in the optics are not restricted. When the ellipsometry method is used, the beam entering the polarizer is preferably natural light or circularly polarized light; in the path from light source SO to the polarizer and the polarizer to the detector SP, it is better to maintain the complete polarization or avoid any polarization sensitive components in the optics; however, the deviations can be completely corrected by using numerical methods.

Next, with the assistance of the figures, the broadband spectroscopic polarimeter based on this embodiment of present invention is described in detail

First Embodiment

Figure 4:
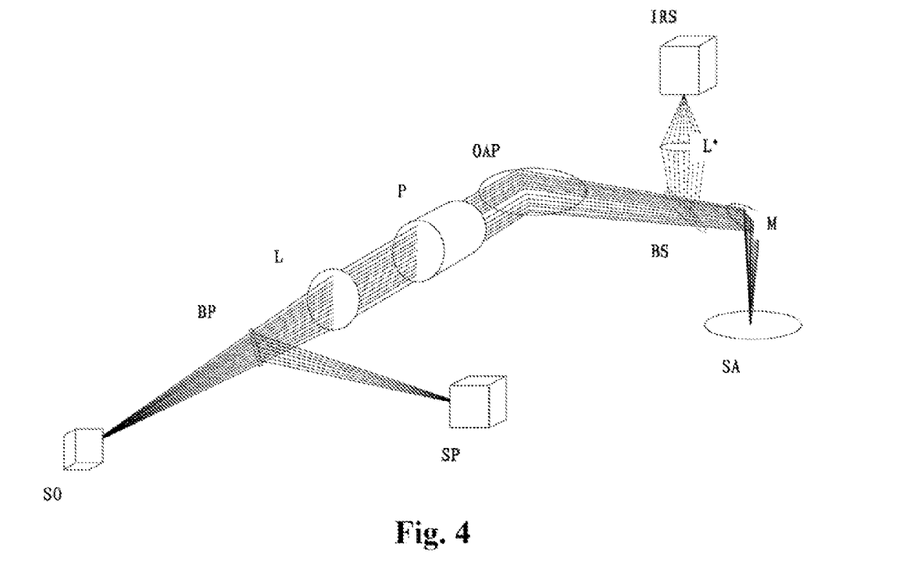
FIG. 4 is a schematic drawing to show the first embodiment of the normal incidence broadband spectroscopic polarimeter of the present invention.

FIG. 4 shows the first embodiment of the normal incidence broadband spectroscopic polarimeter of the present invention. As shown in FIG. 4, the normal incidence broadband spectroscopic polarimeter includes a broadband point light source SO, a splitting element BP, a lens L, an off-axis parabolic mirror OAP, a polarizer P. a broadband spectrometer SP, a flat mirror M, a removable Beam-splitting Plate 135 as well as image recognition system (IRS). The image recognition system IRS includes a lens L', an illumination light source (not shown) and CCD imaging, device (not shown). Broadband point light source SO emits broadband divergence beam, the spectrum of broadband beam is usually in the deep ultraviolet to near infrared range (from about 190 nm to 1100 nm wavelength range). in practice, broadband point light source SO can be a xenon lamp, a deuterium lamp, a tungsten lamp, a halogen lamp, a mercury lamp, a composite broadband light source including deuterium lamp and tungsten lamp, a composite broadband light source including tungsten lamp and halogen lamp, a composite broadband light source including mercury lamp and xenon lamp or a composite broadband light source containing deuterium lamp, tungsten lamp and halogen lamp. The beam emits from the broadband light source can be natural light (i.e., the degree of polarization equal to zero). However, the broadband point source can also be natural point light source with zero degree polarization obtained from a depolarizer (U.S. Pat. No. 6,667,805). Examples for broadband point light source SO include Ocean Optics products HPX-2000, HL-2000 and DH2000, and Hamamatsu company product L11034, L8706, L9841 and L10290, Broadband spectrometer can be charge-coupled device (CCD) or photodiode array (PDA), for example, the Ocean Optics QE65000 spectrometer, or the B & W Teck-Cypher spectrometer.

Figure 5:
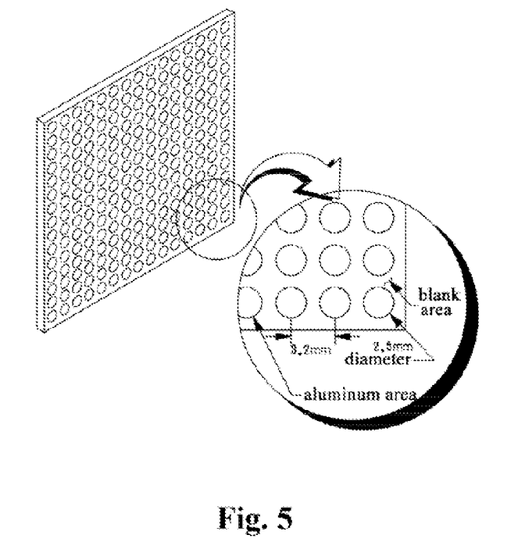
FIG. 5 is a schematic drawing of the Polka-dot Beamsplitter for the first embodiment of the present invention.

The Polka-dot Beamsplitter (i.e., flat mirror coated with periodic metal dots) for the splitting element BP of the embodiment is described next. FIG. 5 shows the plane schematic diagram of the Polka-dot Beamsplitter (taken from www.newport.com). Polka-dot Beamsplitter includes the aluminum area with point patterns and blank area; the form of the pattern can be a variety of shapes and square and round are common. The sheet material for Polka-dot Beamsplitter can be Fused Silica; when light incident on the Polka-dot Beamsplitter, the incident light reflect from the aluminum areas or transmit through the blank areas. Therefore, among the incident light (0-45 degrees angle of incidence) to the aluminizing zone, 50 percent of incident light transmits through the Polka-dot Beamsplitter and 50 percent of incident light reflect from the Polka-dot Beamsplitter. Since aluminum has good reflectivity in a wide spectrum, this Polka-dot Beamsplitter is better than Beam-splitter prism and Beam-splitter plate. Therefore, in this embodiment, the Polka-dot Beamsplitter with significantly superiority, compared to the ordinary beam splitter prism and beam splitter plate, is employed. The examples of Polka-dot Beamsplitter include Edmund Polka-dot Beamsplitter and Newport Polka-dot Beamsplitter.

In FIG. 4, the beam emitted from broadband point light source SO beam propagates in the horizontal plane and then enters the splitting element BP, wherein, 50 percent of incident beam transmit through the splitting element BP and enter the lens L. Since the broadband point source light SO is placed equivalently at the focus of Lens L, the beam from the broadband point source SO is converged into a collimated beam which propagates along the horizontal direction. After passing through polarizer P. the collimated beam enters the off-axis parabolic mirror OAP which deflects it in 90 degrees in the horizontal plane. The beam reflected by the off-axis parabolic mirror OAP is a focused beam with chief ray in the horizontal plane. After reflected by the flat mirror M, the converged beam enters downward to the sample along the vertical direction. The chief ray of beam enters normally and is focused on the sample surface. The light reflected from the sample surface, to flat mirror M. off-axis parabolic mirror OAP, polarizer, and lens L, forms a focused beam. After reflected by splitting element BP, 50 percent of the focused beam enters the broadband spectrometer SP. The broadband spectrometer SP will be placed at the focus of the beam reflected by splitting element BP.

In addition, the tilt angle and/or spatial position of the flat mirror M is adjustable; for example, it can be moved along the propagation direction of the chief ray of the above focused beam reflected from the off-axis parabolic mirror OAP. Similarly, the broadband spectrometer can also include adjustable platform for loading the sample. Based on the above focus principle, the flat mirror M can be adjusted to realize focus. In semiconductor industry, the sample size can be a diameter of 4 inches (100 mm), 6 inches (150 mm), 8 inches (200 mm), or 12 inches (300 mm) wafers. In the flat panel display industry, the samples usually have a size of more than one meter. Due to the reasons such as film stress on wafer, the wafers may be uneven. For a large-scale sample, the sample surface may be distorted, or the sample platform may be uneven. Therefore, each measurement point needs to be refocused when the samples are tested in order to realize better measurement accuracy and achieve high throughput of semiconductor production line.

Before the measurement, the movable Beam-splitting Plate BS is placed into the light path. The probe beam and illumination beam for the pattern recognition system, after reflected by the sample surface and Beam-splitting Plate BS, can both reach the pattern recognition system; then through movable sample platform, the light spot and the measurement pattern can be aligned. From the image clarity of the sample surface focus can be achieved on the sample by referring to the calibrated image recognition system. Therefore, besides observing the changes of light intensity in the spectrometer to achieve focus, the focus can also be obtained by observing the image clarity in the image recognition system in this embodiment. The coexistence of two focusing system improve the focus accuracy of the system and the spot of probe beam and the pattern in sample surface can be aligned. Moreover, during focusing process, the movable beam-splitting plate BS does not need to be adjusted with the position of the flat mirror M. When the beam-splitting plate BS is moved away from the optical path, it does not have any impact on the optical path and the spectrum measurement can be performed.

In this embodiment, if the flat mirror M and off-axis parabolic mirror OAP have the same reflective material and coating structure and meet the conditions that incident angles of the beam are the same and the incident planes are perpendicular to each other, the polarization of the probe beam remains unchanged after passing through the polarizer P when it enters and focuses on the sample SA surface. The angle between linear polarization direction of the probe beam and a fixed direction in sample horizontal plane can be adjusted by rotating the polarizer. The reflected light from the sample, typically elliptically polarized light, remains its polarization unchanged when entering the polarizer P (the polarizer plays the role as analyzer). in present invention, using the two methods as described above, the normal incidence broadband spectroscopic. polarimeter can measure the anisotropic. thin-film sample or non-uniform thin-films sample such as its the critical dimensions (CD) and three-dimensional profile of the periodic pattern of the surface, film thickness and optical constants of the multilayer material. If the flat mirror M and the off-axis parabolic mirror OAP do not have the same reflective material and coating structure and only meet the conditions that the incident plane of beam perpendicular or parallel to each other, the polarization characteristic can remain unchanged only when the probe beam is linearly polarized and the polarization direction is perpendicular or parallel to the incident plane; in this case, the ellipsometry cannot be implemented, but the absolute reflectance measurements can be implemented (please refer to the U.S. Pat. No. 7,505,133B1 for measurement instructions).

In this embodiment, the linear polarization direction of the beam passing through polarizer is determined by the polarizer rotation angle and the beam incident on the polarizer can be an arbitrary polarization state. If the absolute reflectance measurements are chosen, the beam reflected by sample and passed through the polarizer is linearly polarized light; in this process the light reflected by the reference samples and measuring samples experience the same change of polarization state when the beam enters the detector. So it's not required to maintain the polarization and there is no restriction on the polarization sensitivity of optical components. If the ellipsometry method is used, the beam entering the polarizer is preferably natural light or circularly polarized; in the path from light source SO to the polarizer and the polarizer to the detector SP, it is better to maintain the complete polarization or avoid any polarization sensitive components in the optics; but the deviations can be completely corrected by using numerical methods. In this embodiment, in the optical path from light source SO to the polarizer and the polarizer to the detector SP, since Polka-dot Beam-splitter is used, polarization cannot be maintained, requiring a numerical correction before measurements. In addition, in this embodiment, lens L can also be replaced by other forms of focusing unit (for example, off-axis parabolic mirrors or focusing unit consist of several lens, etc.).

In this embodiment, if the flat mirror M and the off-axis parabolic mirror OAP meet the condition that incident angle of the beam is same, the incident angle is not limited to 45 degrees. The implementation can be achieved by off-axis parabolic mirror with incident angle of 7.5 degrees to 45 degrees provided by Edmund optics, or any customized off-axis parabolic mirror with peculiar incident angle. The smaller the incident angle, the smaller the polarization changes caused by the flat mirror reflection and the smaller the polarization state changes due to the flat mirror M and the off-axis parabolic mirror OAP; that is, the situation of 15 degrees incident angle will be better than 45 degrees. Using this embodiment, the normal incidence broadband spectroscopic polarimeter not only can focus by a simple procedure, but also can accurately control the polarization of the probe beam, i.e., the polarization properties of arbitrarily polarized light can be maintained.

Based on this embodiment and the above principle to maintain the polarization properties, other equivalents of this embodiment may be derived.

Second Embodiment

Figure 6:
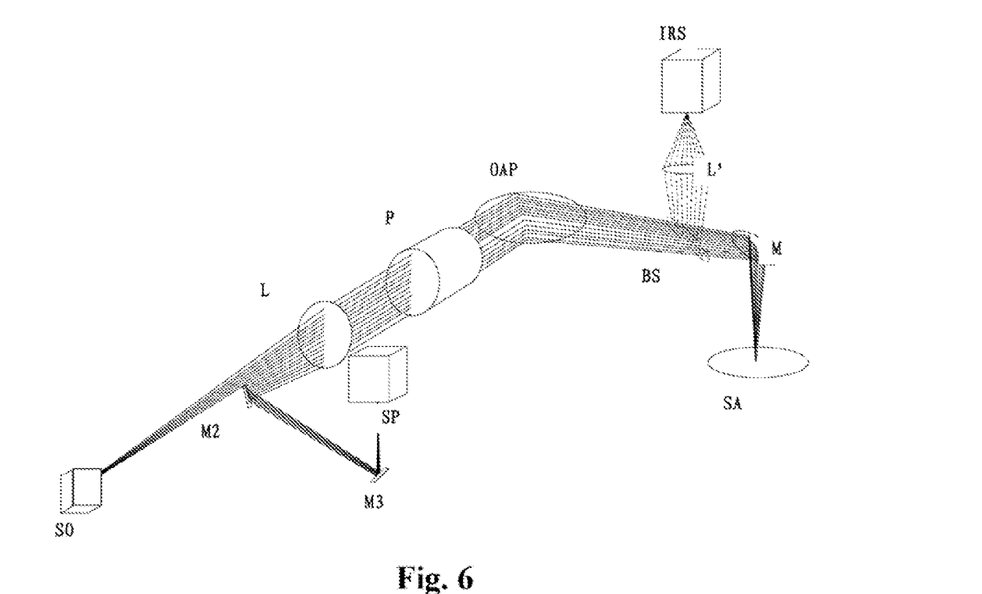
FIG. 6 is a schematic drawing to show the second embodiment of the normal incidence broadband spectroscopic polarimeter of the present invention.

FIG. 6 shows the second embodiment of the normal incidence broadband spectroscopic polarimeter of the present invention. Compared to the spectroscopic polarimeter shown in FIG. 4, the normal incidence broadband spectroscopic polarimeter in this embodiment doesn't contain the splitter element BP, but includes two reflector elements M2 and M3, therein the two reflector elements M2 and M3 are set between lens L and broadband. spectrometer SP respectively. For simplicity, the description of the same characteristics and structures as the first embodiment was omitted. Only the differences between these two embodiments are described.

As shown in FIG. 6, the edge of reflection element M2 is in the light path between light source SO and lens L. The reflector element M3 is placed in the optical path between the broadband spectrometer SP and reflection components M2. The beam from the light source SO propagates in the horizontal plane and then enters the lens L. Since the broadband point light source SO is placed at the focus of lens L, after passing through the lens L, the beam from the broadband point source SO is converged into a collimated beam which propagates along the horizontal direction. After passing through polarizer P. the collimated beam enters the off-axis parabolic mirror OAP which deflects it into 90 degrees in the horizontal plane. The beam reflected by the off-axis parabolic mirror OAP light: is a focused beam with chief ray in the horizontal plane. After reflected by the flat mirror M, the focused beam enters downward to the sample along the vertical direction. The chief ray of focused beam vertically focuses on the sample surface. Broadband spectrometer SP is used to detect the beam which is reflected from the sample, flat mirror M, off-axis parabolic mirror OAP, polarizer P, lens L, reflection element M2 and reflection element M3.

As same as the first embodiment, in this embodiment, if the flat mirror M and off-axis parabolic mirror OAP have the same reflective material and coating structure and meet the conditions that incident angles of the beam are the same and the incident planes are perpendicular to each other, the polarization characteristics of the probe beam remain unchanged after passing through the polarizer P when the beam enters and focuses on sample SA, In addition, if the reflector elements M2 and M3 have the same reflective material and coating structure and meet the conditions that incident angles of the beam are the same and the incident planes are perpendicular to each other, the polarization characteristics of the beam remain unchanged when the beam enters on broadband spectrometer SP after passing through the polarizer P. Moreover, since the lens does not change polarization characteristics of the probe beam, the probe beam polarization remains unchanged when it propagates in the optical path between the polarizer and broadband light source SO. Therefore, in second embodiment, when the light from the light source SO propagates in the optical path between the light source SO and polarizer P, its polarization remains unchanged; after passing through the polarizer P, the polarization characteristics of the beam remains unchanged when it enters broadband spectrometer SP. The beam remains the polarization of natural light from the light source SO before entering to the polarizer; the returned light passing through the polarizer also maintains the linear polarization of reflected beam. This implementation simplifies the polarization sensitivity of the system and only the sensitivity of the detector to linear polarization state is presented. The numerical correction caused by the system polarization sensitivity is simplified in this implementation.

In this embodiment, the angle between linear polarization direction of the probe beam and a fixed direction in sample horizontal plane can be adjusted by rotating the polarizer. When entering and focusing on the sample SA, the polarization of the probe beam remains unchanged after passing through polarizer P. Namely, focusing system and the focusing process do not affect the beam polarization state between the polarizer and the sample surface. The normal incidence broadband spectroscopic polarimeter can be used to measure the properties of the non-uniform thin films sample such as the critical dimensions (CD), three-dimensional profile of the periodic pattern of the surface, film thickness and optical constants of the multilayer material.

Third Embodiment

Figure 7:
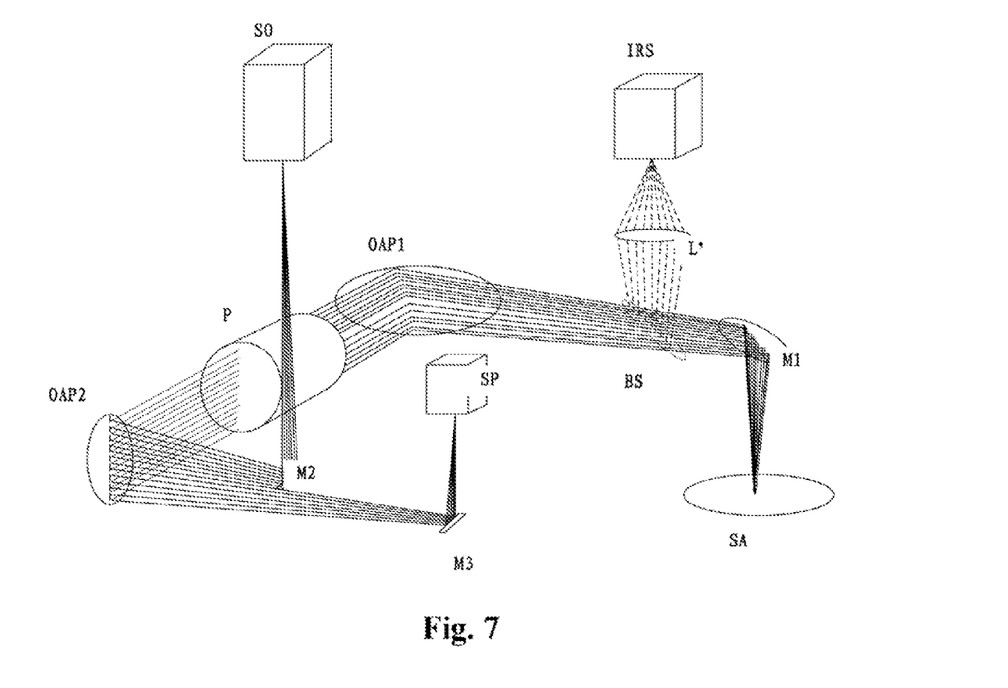
FIG. 7 is a schematic drawing to show the third embodiment of the normal incidence broadband spectroscopic polarimeter of the present invention.

FIG. 7 shows the third embodiment of normal. incidence broadband spectroscopic polarimeter in the present invention. As shown in FIG. 7, the normal incidence broadband spectroscopic polarimeter includes broadband point source SO, first flat mirror M1, first off-axis parabolic mirror OAP1, second off-axis parabolic mirrors OAP2, polarizer P. broadband spectrometer SP, second flat mirrors M2, third flat mirror M3, movable Beam-splitting Plate BS and image recognition system IRS. The image recognition system IRS includes lens L, illumination light source (not shown) and CCD imaging device (not shown). For the simplicity, the same components and functions as the first embodiment are not described in detail.

In this embodiment, the broadband point source SO emits a diverging beam with broadband spectrum which usually ranges from deep ultraviolet to near infrared (about the range from 190 nm to 1100 nm wavelength). The beam vertically propagates to the second flat mirror M2 which reflects it to the horizontal direction of the second off-axis parabolic mirror OAP2. Because the broadband point light source SO is placed at the focal point of the second off-axis parabolic mirror OAP2, the beam from the broadband point light source SO deflects 90 degrees and then forms a collimated beam propagates along the horizontal plane after being reflected by the second off-axis parabolic mirror OAP2. After polarizer P. the collimated beam enters the first off-axis parabolic mirror OAP1 which deflects it 90 degrees in the horizontal plane. The beam reflected by the first off-axis parabolic mirror OAP1 light is a focused beam with chief ray in the horizontal plane. After reflected by the first flat mirror M1, the converging beam is incident down to the sample along the vertical direction. The whole optical system, taking the plane formed by the horizontal symmetry axis of the off-axis parabolic mirrors OAP1 and OAP2 and the first flat mirror M1 as the reference plane, the half parts that are away from the sample and above the reference plane, focuses the probe beam onto the sample surface. The chief ray of focused beam enters normally and focuses on the sample surface. The light reflected from the sample surface, to the first flat mirror M1, the first off-axis parabolic mirror OAP1, polarizer P, the second off-axis parabolic mirror OAP2 and the third flat mirror M3, forms a focused beam. The focused beam enters the broadband spectrometer SP that is located at the focal point. The half parts of the entire optical system, which are close to the sample and are below the reference plane, focus the beam reflected from the sample surface to the spectrometer.

In this embodiment, if the flat mirror M1 and off-axis parabolic mirror OAP1 have the same reflective, material and coating structure and meet the conditions that incident angles of the beam are the same and the incident planes are perpendicular to each other, the polarization of the probe beam remains unchanged when it enters and focuses on the surface of sample SA, after passing through the polarizer P. If the flat mirror M2 and off-axis parabolic mirror OAP2 have the same reflective material and coating structure and meet the conditions that incident angles of the beam are the same and the incident planes are perpendicular to each other, the polarization of the probe beam emitted from light source SO remains unchanged when entering the polarizer surface. If the flat mirror M3 and off-axis parabolic mirror OAP2 have the same reflective material and coating structure and meet the conditions that incident angles of the beam are the same and the incident planes are perpendicular to each other, the polarization of the probe beam remains unchanged when probe beam enters the broadband spectrometer SP, after passing through the polarizer P. Therefore, in this embodiment, the polarization of the probe beam from light source SO remains unchanged after passing through the polarizer P and focusing on the sample SA surface; the polarization of the probe beam from light source SO remains unchanged before entering the polarizer surface; the polarization of natural light from the light source SO are remained before entering the polarizer and the returned light from polarizer also maintains its linear polarization. This implementation simplifies the polarization sensitivity of the system and only the sensitivity of the detector to linear polarization state is presented. The numerical correction caused by the system polarization sensitivity is also simplified in this implementation.

In this embodiment, the angle between linear polarization direction of the probe beam and a fixed direction in sample horizontal plane can be adjusted by rotating the polarizer. When entering and focusing on the surface of sample SA, the polarization of the probe beam remains unchanged after passing through the polarizer P. Namely, focusing system and the focusing process do not affect the beam polarization state between the polarizer and the sample surface. The normal incidence broadband spectroscopic polarimeter can be used to measure the properties of the non-uniform thin films sample such as the critical dimensions (CD), three-dimensional profile of the periodic pattern on the surface, film thickness and optical constants of the multilayer material.

In this embodiment, the second flat mirror M2 can be semicircular flat mirror, or other shapes of flat mirror containing at least one line edge shape.

As in the first embodiment, the normal incidence broadband spectroscopic polarimeter not only can focus by a simple procedure, but also can accurately control the polarization of the probe beam, i.e., the polarization properties of arbitrarily polarized light can be maintained.

All elements in this embodiment are mirrors; in addition to advantages described in the first and second embodiments, chromatic aberration can be eliminated.

Although the flat mirrors in the first and second embodiments and the first flat mirror in the third embodiment can be adjustable or removable, they can also remain fixed. The samples can be placed on a movable or fixed stage. Beam-splitting plate can also be replaced by Polka-dot Beamsplitter or other forms of beam splitter. In addition, the normal incidence broadband spectroscopic polarimeter described in the above embodiments also includes at least one aperture which is located between the polarizer and the sample. It is used to prevent the e light generate by the polarizer being incident onto the sample surface and/or the reflected e light reflecting back to the polarizer. Other apertures may be inserted in any section of the optical path to adjusting the actual numerical aperture of probe beam. The apertures shall be vertical to the chief ray and the central position shall be coincidence with the chief ray.

Moreover, the normal incidence broadband spectroscopic polarimeter can also include computing unit; the computing unit is to do curve regression fit of the mathematical model of reflectivity and calculate the optical constants and film thickness and/or the critical dimension properties or three-dimensional profile of the periodic structure of the sample. Moreover, the normal incidence broadband spectroscopic polarimeter in present invention may also include a rotation control device for polarizer which is used for controlling polarization direction of the polarizer.

The normal incidence broadband spectroscopic polarimeter in present invention is not limited to the specific forms disclosed in the above embodiments; the broadband spectroscopic polarimeter can be all kinds of deformation as long as in accordance with the general concepts describe above. The broadband spectroscopic polarimeter in the present invention can be applied to the measurement of semiconductor thin films, optical masks, metal films, dielectric films, glass (or coating), laser mirrors, thickness and optical constants of organic thin film, and critical dimension and three-dimensional profile of periodic structures consisting of these materials, in particular, can be applied to measure all dimensions of three-dimensional structures with one and two dimensional periodicity and formed by multilayer films in a plane and optical constants of layers of material. In addition, the broadband spectroscopic polarimeter in present invention can achieve both auto-focus and manual focus.

This invention is not limited to the disclosed exemplary embodiments. The scope of the claims shall have wider range of interpretation, including all such modifications and equivalent structures and functions based on the concepts described above.

What is claimed is:

1. A normal incidence broadband spectroscopic polarimeter comprising a light source, a beam splitting element, a focusing unit, a polarizer, a first curved reflector element, a first flat reflector element and a detection unit, wherein:
   the beam splitting element is set in an optical path between the light source and the focusing unit, and is used to pass through part of the beam from the light source before incident on the focusing unit, and to receive a beam that is reflected from a sample and is in turn reflected by the flat reflector element, the first curved reflector element, goes through the polarizer and the focusing unit, and then to reflect the beam to the detection unit;
   the focusing unit is used to receive the beam passing through the beam splitting element and to converge the beam into a collimated beam;
   the polarizer set between the focusing unit and the first curved reflector element is used to pass through the collimated beam to the first curved reflector element;
   the first curved reflector element is used to receive the collimated beam of the polarizer and converge the beam into a focused beam;
   the first flat reflector element is used to receive the focused beam and reflect the focused beam and make it normal incidence onto the sample, as well as focus on the sample; and
   the detection unit is used to detect a beam that is reflected from the sample and is in turn reflected by the first flat reflector element, the first curved reflector element, and goes through the polarizer and the focusing unit and is then reflected by the beam splitting element.

2. The normal incidence broadband spectroscopic polarimeter according to claim 1, wherein the first flat reflector element and first curved reflector element have the same reflective materials and coating structures and meet the conditions that incident angles of beam are the same and the incident planes are perpendicular to each other.

3. The normal incidence broadband spectroscopic polarimeter according to claim 1, wherein the beam splitting element is a Beam-splitting plate, a Beam-splitting prism, a Polka-dot Beamsplitter, or Pellicle Beamsplitter.

4. The normal incidence broadband spectroscopic polarimeter according to claim 3, wherein the focusing unit is at least one lens or at least one curved reflector mirror.

5. The normal incidence broadband spectroscopic polarimeter according to claim 1, wherein the beam splitting element is a second reflector element, the edge of which is in the optical path.

6. The normal incidence broadband spectroscopic polarimeter according to claim 5, wherein the focusing unit is at least one lens.

7. The normal incidence broadband spectroscopic polarimeter according to claim 6, further comprising a third reflector element which is set in an optical path between the detection unit and the second reflector element, wherein:
the detection unit is used to detect a beam that is reflected from the sample and is in turn reflected by the first flat reflector element, the first curved reflector element, goes through the polarizer, the at least one lens, the second reflector element and the third reflector element;
the first flat reflector element and the first curved reflector element have the same reflective material and coating structure and meet the conditions that the incident angles of beam are the same and the incident planes are perpendicular to each other; and
the second reflector element and the third reflector element have the same reflective material and coating structure and meet the conditions that incident angles of beam are the same and the incident planes are perpendicular to each other.

8. The normal incidence broadband spectroscopic polarimeter according to claim 5, wherein the focusing unit is a second curved reflector element.

9. The normal incidence broadband spectroscopic polarimeter according to claim 8, wherein the first flat reflector element and the first curved reflector element have the same reflective material and coating structure and meet the conditions that the incident angles of beam are the same and the incident planes are perpendicular to each other, and
the second reflector element and the second curved reflector element have the same reflective material and coating structure and meet the conditions that the incident angles of beam are the same and the incident planes are perpendicular to each other.

10. The normal incidence broadband spectroscopic polarimeter according to claim 9, further comprising a third reflector element which is set in an optical path between the detection unit and the second curved reflector element, wherein:
the detection unit is used to detect a beam that is reflected from the sample and in turn goes through the first flat reflector element, the first curved reflector element, the polarizer, the second curved reflector element and the third reflector element; and
the third reflector element and the second curved reflector element have the same reflective material and coating structure and meet the conditions that the incident angles of beam are the same and the incident planes are perpendicular to each other.

11. The normal incidence broadband spectroscopic polarimeter according to claim 5, wherein the second reflector element is a reflector element with at least one line edge which cross the chief ray of optical path.

12. The normal incidence broadband spectroscopic polarimeter according to claim 1, wherein the first curved reflector element is off-axis parabolic reflector element or toroidal reflector element.

13. The normal incidence broadband spectroscopic polarimeter according to claim 8, wherein the first curved reflector element and the second curved reflector element are off-axis parabolic reflector element or toroidal reflector element.

14. The normal incidence broadband spectroscopic polarimeter according to claim 1, wherein the tilt angle and/or spatial position of the first flat reflector element are adjustable.

15. The normal incidence broadband spectroscopic polarimeter according to claim 1, wherein the first flat reflector element can move along the propagation direction of the chief ray of the focused beam.

16. The normal incidence broadband spectroscopic polarimeter according to claim 1, further comprising a sample platform which is adjustable and is used for loading the sample.

17. The normal incidence broadband spectroscopic polarimeter according to claim 1, further comprising a movable beam splitter and image recognition system, wherein:
the image recognition system includes a lens, an illumination light source and a CCD imaging device;
the movable beam splitter is used for reflecting a sample illuminating beam provide by the image recognition system to the surface of the sample and reflecting the reflected beam from the surface of the sample to the CCD imaging device; and
focusing can be adjusted through observing light intensity of the detection unit and/or image clarity of the pattern in the image recognition system.

18. The normal incidence broadband spectroscopic polarimeter according to claim 1, further comprising at least one aperture, the at least one aperture locates between the polarizer and the sample, the at least one aperture is used for avoiding the e light generated by passing through the polarizer from being incident on the surface of the sample and/or the reflected e light from reflecting back to the polarizer.

19. The normal incidence broadband spectroscopic polarimeter according to claim 1, further comprising apertures, which can be placed in any section of an optical path of the entire optical system.

20. The normal incidence broadband spectroscopic polarimeter according to claim 1, wherein the light source is a light source includes multiple wavelengths of light.

21. The normal incidence broadband spectroscopic polarimeter according to claim 1, wherein the light source is a xenon lamp, a deuterium lamp, a tungsten lamp, a halogen lamp, a mercury lamp, a composite broadband light source including deuterium lamps and tungsten lamps, a composite broadband light source including tungsten lamps and halogen lamps, a composite broadband light source including mercury lamps and xenon lamps or a composite broadband light source containing deuterium, tungsten and halogen, or, said light source is a point light source of natural light with zero degree polarization got from depolarizer.

22. The normal incidence broadband spectroscopic polarimeter according to claim 1, wherein the polarizer is a Rochon prism polarizer.

23. The normal incidence broadband spectroscopic polarimeter according to claim 1, further comprising a rotation control device, wherein the rotation control device is used to control polarization direction of the polarizer.

24. The normal incidence broadband spectroscopic polarimeter according to claim 1, wherein the detection unit is a spectrometer.

25. The normal incidence broadband spectroscopic polarimeter according to claim 1, further comprising a computing unit, wherein: the computing unit is used to calculate the optical constants of sample material, film thickness, and/or to analyze the critical dimension properties or three-dimensional profiles of the periodic structure of the sample.

26. An optical measurement system, comprising a normal incidence broadband spectroscopic polarimeter, comprising a light source, a beam splitting element, a focusing unit, a polarizer, a first curved reflector element, a first flat reflector element and a detection unit, wherein:
the beam splitting element is set in an optical path between the light source and the focusing unit, and is used to pass through part of the beam from the light source before incident on the focusing unit, and to receive a beam that is reflected from a sample and is in turn reflected by the flat reflector element, the first curved reflector element, goes through the polarizer and the focusing unit, and then to reflect the beam to the detection unit;

the focusing unit is used to receive the beam passing through the beam splitting element and to converge the beam into a collimated beam;

the polarizer set between the focusing unit and the first curved reflector element is used to pass through the collimated beam to the first curved reflector element;

the first curved reflector element is used to receive the collimated beam of the polarizer and converge the beam into a focused beam;

the first flat reflector element is used to receive the focused beam and reflect the focused beam and make it normal incidence onto the sample, as well as focus on the sample; and the detection unit is used to detect a beam that is reflected from the sample and is in turn reflected by the first flat reflector element, the first curved reflector element, and goes through the polarizer and the focusing unit and is then reflected by the beam splitting element.

* * * * *